(12) United States Patent
Kuribayashi et al.

(10) Patent No.: US 6,915,159 B1
(45) Date of Patent: Jul. 5, 2005

(54) ELECTRODE STRUCTURE FOR IONTOPHORESIS DEVICE AND METHOD OF PRODUCING THE SAME

(75) Inventors: Mitsuru Kuribayashi, Tsukuba (JP); Hiroyuki Maeda, Tsukuba (JP); Nobuhiro Koga, Tsukuba (JP); Naruhito Higo, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/807,832

(22) PCT Filed: May 10, 2000

(86) PCT No.: PCT/JP00/02967

§ 371 (c)(1),
(2), (4) Date: Nov. 13, 2001

(87) PCT Pub. No.: WO00/69514

PCT Pub. Date: Nov. 23, 2000

(30) Foreign Application Priority Data

May 13, 1999 (JP) .......................................... 11/132676

(51) Int. Cl.⁷ ................................................. A61N 1/30
(52) U.S. Cl. ....................................................... 604/20
(58) Field of Search ..................... 604/20, 19, 890.1, 604/289

(56) References Cited

PUBLICATIONS

Machine translation of WO 96/10439.*
Machine translation of WO 97/06847.*
Abstract of WO 96/10439.*
Abstract of WO 97/06847.*

* cited by examiner

Primary Examiner—Manuel Mendez
(74) Attorney, Agent, or Firm—Townsend & Banta

(57) ABSTRACT

The invention is to provide an electrode structure of an iontophoresis device and a method of producing the same, excellent in an economical property, an operational property, stability and safety. The electrode structure for the iontophoresis device comprises a backing having a substrate film (1) having a molding portion, an anode side and a cathode side electrode layers (14), (15) formed passing the outer circumferential portion from the inner bottom of the molding portion, and an insulating layer 3 formed in the outer circumferential portion of the molding portion. The molding portion of the backing has a dent portion and an anode side and a cathode side conductive layers (12), (13) are separately installed therein. A cover member (8) is installed to seal between these conductive layers (12), (13) and the insulating layer (3). An adhesive sheet (10) for attachment to the skin is provided to the rear face of the substrate film (1) and a liner (16) for the adhesive sheet is provided on the cover member (8).

16 Claims, 7 Drawing Sheets

(a)                    (b)

(a)                    (b)

(a)

(b)

(c)

(a)

(b)

ELECTRODE STRUCTURE FOR IONTOPHORESIS DEVICE AND METHOD OF PRODUCING THE SAME

TECHNICAL FIELD

The present invention relates to an iontophoresis device suitable for transdermal and transmucosal application. More particularly, in an electrode structure disposable for an iontophoresis device, the invention relates to an electrode structure for an iontophoresis device as a mass production type, whose connection manner with an electric current output portion is simple and further which is capable of keeping the conductive layer in the sealed state and possible to be easily constituted, and relates to a method of producing the electrode structure.

BACKGROUND ART

Iontophoresis is to administer a drug through the skin or the mucosa by applying voltage to the skin or the mucosa and electrically causing migration of an ionic drug. An iontophoresis device is so constituted as to carry out medical care by sticking electrodes for an anode and a cathode for iontophoresis to skin at a predetermined distance from each other and leading the electric current generated in an electric current generator to the electrodes.

Further, the iontophoresis device has a structure of combination of layers for storing a pharmaceutical agent and the electrodes and a previously planed predetermined quantity of a pharmaceutically effective component and a variety of additives besides the component based on necessity are sealed for the purpose to keep the internal concentration of the drug in blood for a predetermined time.

Regarding the basic structure of the iontophoresis device with the above described constitution, many have been proposed for the purpose of improvement of the capability, operability and the economical properties. As exemplary ones, the techniques disclosed in National Publication of International Patent Application Nos. 7-507464, 8-503875, 8-505303, 8-508915, 10-509334, Patent No. 2542792, Japanese Patent Publication No. 6-47014, Japanese Patent Laid-Open Nos. 8-229140, 8-196644, 9-201420and the like, are known. However, it is difficult to practically commercialize this kind of device. One of the reasons for that is because of the complicated electrode structure of the iontophoresis device and the high cost following the complication. Further, as the factors of the structure complication, the retaining form of the drug storage layer, the retaining member structure for the layer and the conducting form for transmitting the electric current to the drug storage layer, are exemplified.

For example, in National Publication of International Patent Application No. 7-507464, proposed is a method of impregnating the drug retaining layer by disposing a capsule or porch enclosing water or an electrolytic solution in the upper portion of the electrode structure and breaking the capsule or the porch at the using time. The technique is for a produced agent of a type to be dissolved in use for the purpose of using a drug unstable in water. However, owing to its complicated structure, mass production is supposed to be difficult and further no joining means between the electrodes and the electric current output portion is disclosed to make the technique insufficient in practical application. Further, in Japanese Patent Publication No. 6-47014, disclosed is an apparatus in which the complicated electric circuits are simplified by installing an anode, a cathode, an electric current output portion and a drug storage layer all in a backing processed by molding and making the backing material be a conductive plastic. However, in this technique, there is a risk of pharmaceutical agent leakage from the drug storage layer in terms of the structure and the storage stability is also a problem.

Further, both of the above described two examples of the techniques, cannot be said to be economical structure since both internally comprise electric current output portions. Hence, taking the economical property into consideration, proposed is an apparatus in which an electric current output portion to be used repeatedly and disposable portions (electrode portions and drug storage portions) are separated. In the case of this apparatus, what important is the method how to connect the electrode portions neighboring the drug storage portions and the electric current output portion for supplying electric current to the electrode portions. For example, Japanese Patent Laid-Open No. 8-229140 discloses an agent of the type to be dissolved at the using time. In this agent, lead portions of the electrode layers are led out a backing by forming holes in the backing so as to be connected with the electric current output portion. The electrode layers are the types incorporated in the molded backing and thus are not to be said to be suitable for mass production.

Further, those disclosed in the Japanese Patent Laid-Open No.8-196644 and Japanese Patent Laid-Open No. 9-201420 employ convexity terminals as connection means for the electrode layers and the electric current output portion. This form is widely employed as the constitution for electrodes for electrocardiogram and low frequency. However, from the manufacturing aspect, holes have to be formed in the backing to insert the convexity terminals, so that this form is not suitable for mass production and further since there is a risk of leakage of the components of the drug storage layer out of the terminal installation portion, there occurs a problem in storage. Further, from the viewpoint of use feeling, if convexity terminals with no flexibility are installed, the entire flexibility of the backing is deteriorated and simultaneously the property of attaching to the skin is also deteriorated. Further, it is reported that direct electric current flows from the terminal installation portion to irritate the skin and insulation covers for preventing direct electric current are required. Further, although using no such convexity terminals as described above, a structure body disclosed in Japanese Patent Laid-Open No. 10-234864 is provided with energizing hole portion in a recessed portion of a cup-like supporting body in order to connect an electrolytic layer disposed in the inside of the supporting body and an electrode layer formed in the outside and also, in this case, there is probability to cause a problem similar to those described above.

Further, National Publication of International Patent Application No.10-509334 discloses a connection method using no terminals for connection. The form is composed by providing the connection function in the electric current output portion side and sandwiching lead portion of a plane-type backing in which electrode are printed with the electric current output portion. This technique is advanced in the operational property, however the form of the drug storage layer is restricted in the point that the backing is plane-type one. For example, it is expected to be difficult to store a liquid or a gel with water-evaporating property in state as it is previously installed and in the case of the drug storage layer in such a form, it is forcibly required for the drug storage layer to be wrapped separately. Further, Japanese Patent Laid-Open No. 11-54855 discloses an electronic portion to be employed as an electrode of a low frequency therapeutic care apparatus by packing an electrolytic gel in a recessed portion in which an electric conductive pattern is printed. Further, National Publication of International Patent Application No. 10-509694 discloses a method for forming a patch for ion penetration curing in an inert atmosphere and wrapping it in order to prolong the storage period.

Regarding a conventional iontophoresis device, there are the following problems.

(1) The apparatus in which an anode, a cathode, an electric current output portion and a drug storage layer are incorporated in one packing has a complicated structure, so that mass production is made difficult and the cost is also high. Further, since the electric current output portion cannot be used repeatedly, the apparatus is not economical.

(2) In the case of an apparatus in which an electric current output portion to be used repeatedly and disposable portions (electrode portions and drug storage portions) are separated, there is a problem to be solved in the connection means between the electrode portions in a backing and the electric current output portion. For example, in the case of using terminals in an apparatus in which a conductive gel is packed in a molded processed portion, leakage and evaporation of a drug-stored component are probable to take place. Further, depending on the connection means, the cost becomes high in some cases.

(3) In some connection means of electrode portions and an electric current output portion, it is probable to deteriorate the flexibility of the entire body of the apparatus and to cause electric irritation in a human body.

(4) In the case of plane-type backing in which electrodes are printed, the form of the drug storage layer is restricted and in the case where a drug storage layer with a high water content is formed, the molded backing has to have high sealing property, however heating is required at the time of the molding process, the electrode layers are significantly affected and it is probable for the electrode layers to be disconnected. Further, in the case of an electrode in which an electrolytic gel is simply packed in a recessed portion bearing a printed conductive pattern, leakage and evaporation of a drug-stored component are probable to take place and batch production in an inert atmosphere lead to cost up.

DISCLOSURE OF THE INVENTION

An object of the invention is to solve the above described problems and to provide an electrode structure for an iontophoresis device and a method of producing the same, excellent in an economical property, an operational property, stability and safety.

Inventors of the present invention have enthusiastically investigated to solve the above described problems and consequently found that the connection of electrode portions and an electric current output portion can easily be connected with a good operational property, the drug stability can be guaranteed owing to the high sealing property of conductive layers and further excellent economical properties and safety can be provided by the following electrode structure for an iontophoresis device and the method of producing it and finally achieve the invention.

That is, the electrode structure for an iontophoresis device according to the invention comprises a backing having a substrate film having a molding portion, an electrode layer formed passing the outer circumferential portion from the inner bottom of the molding portion, and an insulating layer formed at least the outer circumferential portion of the molding portion and also in the upper portion of the electrode layer; a conductive layer formed in the molding portion; and a cover member for protecting the conductive layer. In this case, an adhesive sheet for holding the electrode structure in the skin or the like in the contacting state is installed in the rear face of the substrate film of the backing.

The sinking depth in the molding portion of the substrate film is preferably in a range of 0.5 mm to 7.5 mm and more preferably 1.0 mm to 5.0 mm and the molding angle is preferably in a range of 5° to 700° and more preferably 30° to 60°. Incidentally, the term "molding angle" in this specification means the inclination of a side face of the molding portion to the substrate face before the molding. The cover member is to seal the conductive layer between the insulating layer and itself in a separable manner. In this case, the separation mechanism between the insulating layer and the cover member is preferably interfacial separation and the 180 degree-portioning strength between them is preferable to be set in a range of 100 g to 1.500 g per 15 mm and more preferably 200 g to 1,000 g per 15 mm.

Further, the electrode structure for the iontophoresis device according to the invention comprises a backing having a substrate film provided with a molding portion having a dent, a flange portion formed in the outer circumferential portion of the molding portion, and a lead portion led out of the flange portion, an electrode layer formed from the inner bottom of the molding portion to the lead portion through the flange portion, and an insulating layer formed in at least the flange portion and also in the upper portion of the electrode layer; a conductive layer formed in the molding portion; and a cover member for sealing the backing between the insulating layer and the material itself in a separable manner. In this case, the lead portion formed in the electrode layer is so composed as to be connected with the clip portion of a connection cord or so composed as to have an insertion inlet for a connector such as a conductive snap connector.

The method of producing the electrode structure for an iontophoresis device according to the invention comprises (a) a step of printing a conductive layer and an insulating layer on a substrate film, (b) a step of forming a molding portion in the substrate film in a manner that the insulating layer is positioned at least in the outer circumferential portion, (c) a step of disposing a conductive layer in the molding portion, (d) a step of supplying a cover member to the substrate film and sealing between the insulating layer and the cover member, and (e) a step of cutting the substrate film and the cover member in a predetermined shape. In this case, cutting of the substrate film and the cover member may be carried out in the same and single step or in separate steps. In the case of cutting in separate steps, at first the substrate film is cut and the cover member is supplied to the resulting cut substrate film and then the cover member is cut. Also, at least the forgoing (b) to (e) steps are better to be carried out in a continuous line. Additionally, in this manufacture method, it is optional to add a step of supplying an adhesive sheet to the rear face of the substrate film and cutting the sheet into a predetermined shape.

The step of forming the molding portion is carried out while a convexity portion of a press die being butted to at least the electrode layer on the substrate film. At that time, molding is preferable to be carried out by cold processing at a temperature lower than the thermal deformation. Further, the step of disposing the conductive layer to the molding portion may include a step of promoting gelling of conductive gel composing the conductive layer. The process is practically to promote gelling by physical cross-linking by cooling or chemical cross-linking by light or heat.

BEST MODE FOR CARRYING OUT THE INVENTION

Figure 4:
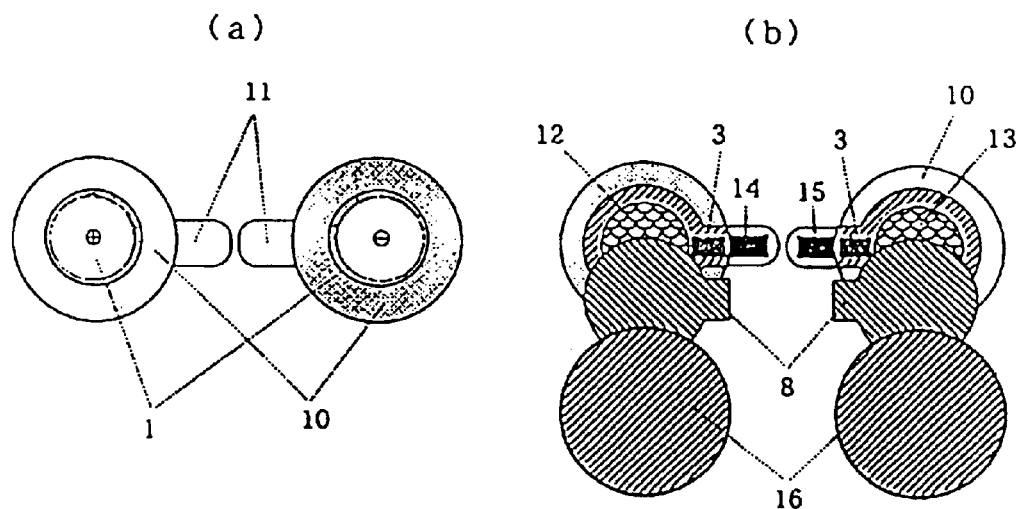
FIG. 4 shows an outline of a separation type electrode structure (Ib-1) of an iontophoresis device according to the invention, (a) shows the front view and (b) shows the inside view.
Figure 5:
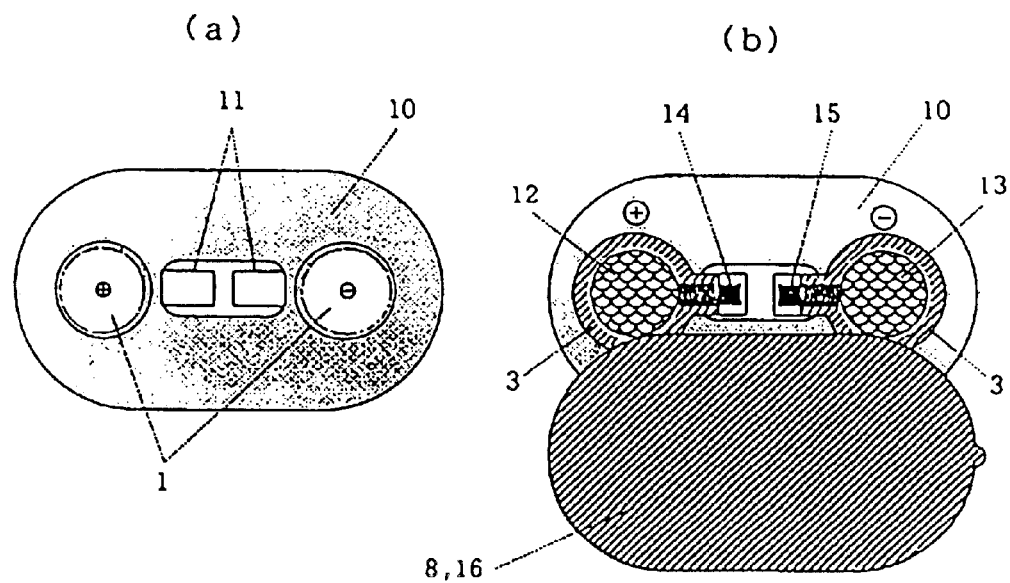
FIG. 5 shows an outline of a separation type electrode structure (Ib-2) of an iontophoresis device according to the invention, (a) shows the front view and (b) shows the inside view.
Figure 6:
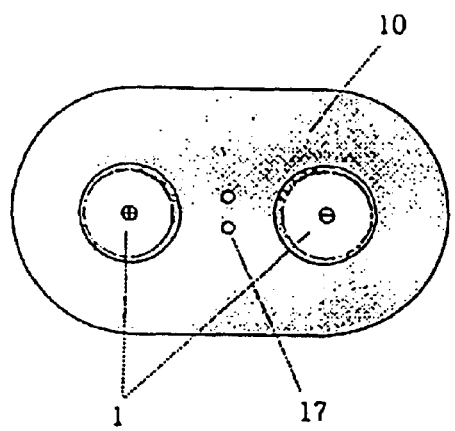
FIG. 6 shows an outline of an integrated type electrode structure (Ib-3) of an iontophoresis device according to the invention, (a) shows the front view, (b) shows the inside view, and (c) shows a cross-sectional view.
Figure 6:
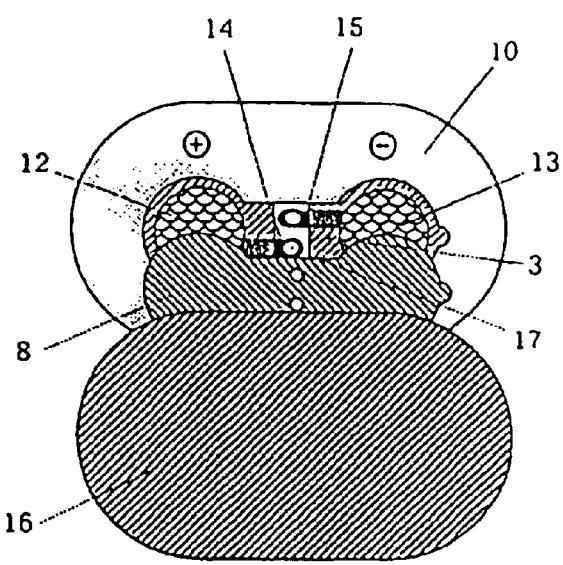
Figure 6:
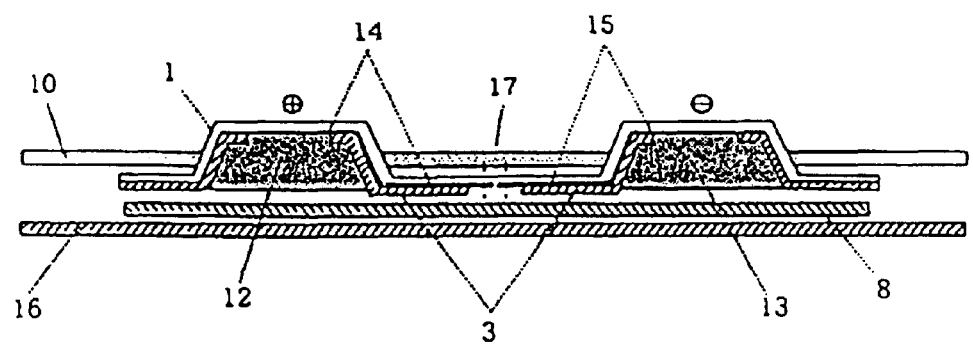

An electrode structure of an iontophoresis device according to the invention is composed as shown in, for example, FIG. 4 to FIG. 6. FIG. 4 shows a separation type electrode structure (Ib-1) and (a) shows the front view and (b) shows the inside view. FIG. 5 shows another separation type electrode structure (Ib-2), (a) shows the front view and (b) shows the inside view. FIG. 6 shows an integrated type electrode structure (Ib-3), (a) shows the front view, (b) shows the inside view and (c) shows a cross-sectional view.

Figure 3:
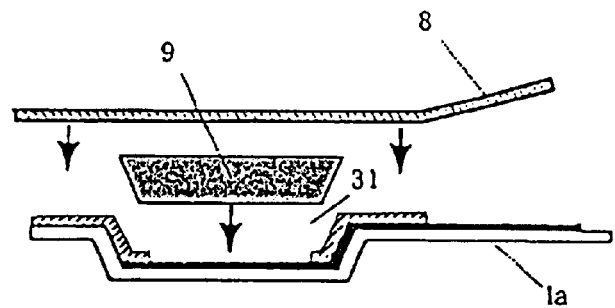
FIG. 3 is a schematic figure showing the basic embodiment of an electrode structure (Ib) of an iontophoresis device according to the invention.

The foregoing respective electrode structure has the electrode structure (Ib) shown in FIG. 3 as the basic constitution. As shown in the figure, a molding portion 31 is formed in a backing (Ia) and a conductive layer 9 is placed therein, a cover member 8 is installed further thereon, and consequently, the backing is sealed.

Figure 1:
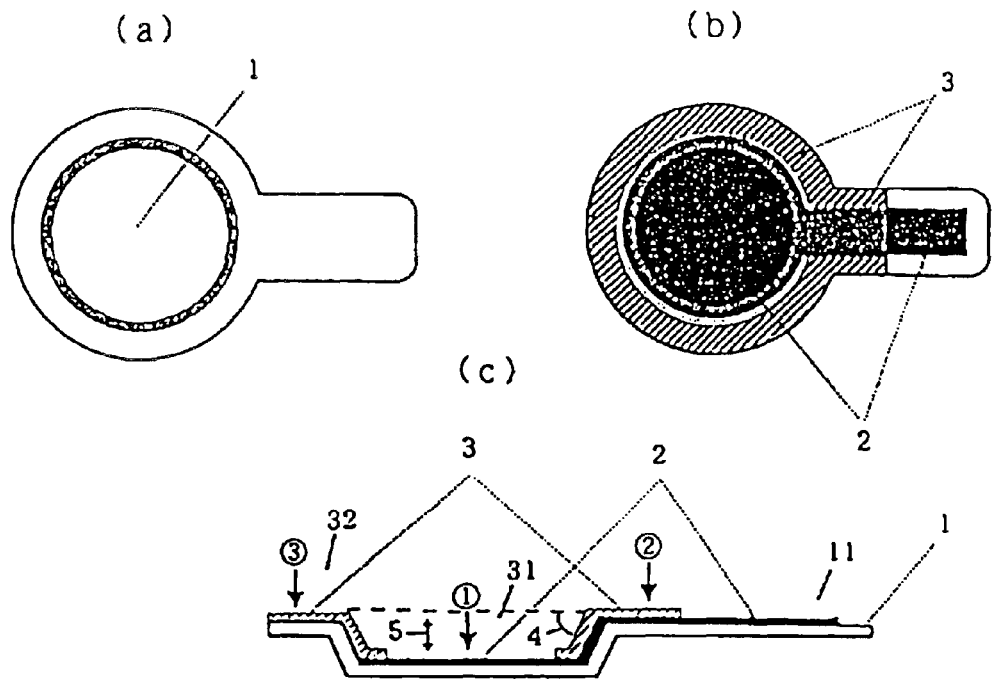
FIG. 1 shows an outline of a backing (Ia) of an iontophoresis device according to the invention, (a) is the front view, (b) is the back side view, and (c) is a cross-sectional view.
Figure 2:
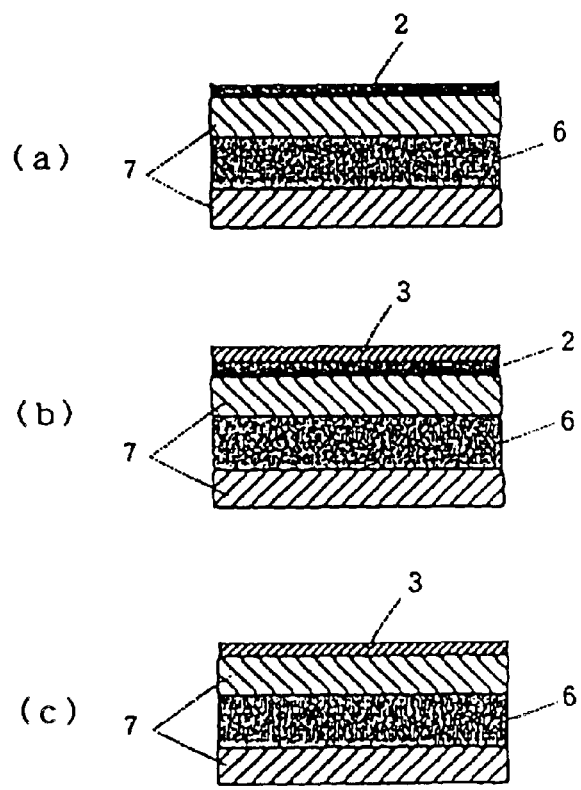
FIG. 2 shows a partial cross-sectional view of a backing (Ia) of an iontophoresis device according to the invention, (a) shows section ①of FIG. 1, (b) shows section ②, and (c) shows section ③.

FIG. 1 shows the backing (Ia) and (a) shows a front view, (b) shows a rear side view, and (c) shows a cross-sectional view. FIG. 2 shows a partial cross-sectional view of the backing, (a) shows section ①, (b) shows section ②, and (c) shows section ③ of the FIG. 1 (c). Their constitutions will be described more particularly in examples and before that, the materials or the like to be employed for the respective portions will be described below.

At first, as the substrate film 1 for the backing, a laminate product of a plastic film 7 non-permeable to pharmaceutical components and a metal foil 6 may be used.

As examples of the plastic film 7, a film, a sheet, and a foamed body made of synthetic resin such as polyethylene, polypropylene, polyethylene terephthalate, polyvinyl chloride, polyvinylidene chloride, plasticized vinyl acetate copolymer, plasticized vinly acetate-vinyl chloride copolymer, polyamide, cellophane, acetyl cellulose, ethyl cellulose, polyester, polycarbonate, polystyrene, polyurethane, polybutadiene, polyimide, polyacrylonitrile, polyisoprene, polystyrenederivative, ethylene-vinylacetate copolymer, ethylene-polyvinyl alcohol copolymer, fluoro resin, acrylic resin, epoxy resin and the like, may be used solely or in form of a plurality of layers. Among them, most preferable is a polyester-based film represented with polyethylene terephthalate.

On the other hand, as examples of the metal foil 6, metal foils such as a copper foil, an aluminum foil, a tin foil, a gold foil, a lead foil and their alloy foils may be used and an aluminum foil is most preferable.

Further, as the substrate film 1, a laminate with a non-woven fabric or a synthetic paper sheet, an aluminum-evaporated one, a ceramic-coated one, and also a sand mat-treated one, may be used.

The backing (Ia) in the invention is a substrate produced without requiring heating at the time of molding into a sheet and having high uniformity as a molding product. The molding. product also has a high bending property and a good shape retaining property for retaining the bent state, so that the close adhesion is made possible at the time of attachment to the skin. On the other hand, since the film has stiffness sufficient not to deteriorate the molding uniformity, the conductive layer internally formed in the molding portion is not broken by external impacts. Incidentally, in the constitution of the substrate film 1 in the invention, the metal foil 6 is a substrate showing the characteristics of the high bending property and the shape retaining property, whereas the plastic film 7 is a substrate showing the stiffness and the molding uniformity of the molded product. In the invention, by adjusting the constitution ratio of both substrates having mutually contrary properties, it is made possible to provide the obtained substrate with properties of both. Although the constitution ratio of both substrates differs depending on the substrate components, generally, the constitution ratio of the plastic film to the metal foil 6 in the substrate film 1 is 1.0, preferably 1.2, and more preferably 1.5 for the lower limit, and 4.0, preferably 3.0, and more preferably 2.5 for the upper limit.

If the constitution ratio is less than 1.0, the properties of the metal foil 6 become so dominant to make the molding product have no stiffness and molding uniformity and if the constitution ratio is higher than 4.0, the stiffness of the plastic film 7 tends to be dominant over the bending property and the shape retaining property of the metal foil 6 and consequently, the attachment property to the skin is deteriorated and further heating is required for the sheet molding and both cases are thus undesirable.

Further, the laminate constitution of the metal foil 6 and the plastic film 7 is not particularly restricted except the insulating plastic film is layered in the side where an electrode layer 2 is printed, however the constitution is preferable to be formed in a constitution sandwiching the metal foil 6 with plastic films 7 just like a plastic film (in the electrode layer side)/a metal foil/a plastic film. If the metal foil is adjacent to the electrode layer 2, since it is a conductor and possible to be corroded, it is impossible to print the electrode layer directly on the metal foil and further since the conductive layer is brought into contact with the metal foil, corrosion takes place in the metal foil. Further, if the metal foil 6 is in the outermost side of the electrode structure, corrosion takes place with the lapse of time and a cutting burr is formed at the time of processing. Consequently, it is not preferable to expose the metal foil 6 in the laminate constitution.

Regarding the entire thickness of the substrate film 1 for backing, the lower limit is 100 $\mu$m, preferably 120 $\mu$m, and more preferable 150 $\mu$m and the upper limit is 300 $\mu$m, preferably 250 $\mu$m, and more preferable 200 $\mu$m. In the case where the thickness is thinner than 100 $\mu$m, although the bending property is provided, the stiffness becomes too low to protect the conductive layer internally formed in the molding portion and in the case where the thickness is thicker than 300 $\mu$m, if constitution ratio of the plastic film 7 is too high, the stiffness becomes too strong and it is not preferable from the viewpoint of the attachment to the skin and the molding processibility. As a countermeasure to deal with that, it is supposedly possible to heighten the constitution ratio of the metal foil 6, however in that case, the material cost will be increased and thus it is not preferable.

The thickness of the metal foil 6 is preferably 15 $\mu$m or more except the case where steam barrier treatment is performed to the plastic film 7. As a laminating method for the substrate film 1 for backing in the invention, a conventional technique is applicable and examples are lamination methods such as wet lamination, dry lamination, thermoplastic lamination, pressure lamination, extrusion lamination and the like. Incidentally, if the lamination thickness is thin, a coating method is also possible to be employed.

The electrode layer 2 in the invention, any structure can be used if it has a conventional well-known electrode structure, and usable are, for example, platinum black, titanium, carbon, aluminum, iron, lead, carbon conductive rubber, conductive resin, a platinum electrode, a silver electrode, a silver chloride electrode and the like and they may be used solely or a mixture and especially desirable ones are the platinum electrode, the silver electrode, the silver chloride electrode and the like.

As the method for layering the electrode layer 2 to the backing, a method by applying a conductive ink mixed with an electrically conductive material to the substrate film for the backing using a conventional printing technique such as screen printing and gravure printing and drying the ink, a method by extending the foregoing electrode material and fixing it, a method by evaporating the foregoing electrode material, a method by photo-etching the foregoing electrode material to produce it and the like, may be used.

Further, an insulating layer 3 may be layered further on the electrode layer 2 in the portion where the electrode layer 2 is possible to be brought into contact with the skin.

The insulating layer 3 in the invention is formed using generally a laminate of an insulating sheet or by coating with insulating resin. The component to be used are not particularly restricted if they are used commonly for therapeutic care and preferable are those excellent in the waterproof and oil-proof. Further, taking the heat-sealing property in relation to the cover member, it is preferable to select a material capable of sealing heat. For example, synthetic resin and films of polyethylene, polypropylene, polyethylene terephthalate, polyvinyl chloride, poly-vinylidene chloride, polystyrene, polyurethane, ethylene-vinyl acetate copolymer, ethylene-polyvinyl alcohol copolymer, epoxy resin and the like, may be used solely or in form of a plurality of layers. Among them, most preferable is a polyester resin- represented with polyethylene terephthalate. In the case of coating with the insulating resin, an insulating ink can be used while being mixed with a pigment and fillers based on necessity. Further, the thickness of the insulating layer is preferable 5 to 30 $\mu$m and especially preferably 10 to 20 $\mu$m.

Next, a liner and a cover member in an iontophoresis device of the invention may be any if they are made of water-impermeable materials. As the liner 16 for an adhesive sheet 10, usable are an aluminum foil, a polyester film, a polypropylene film, a polyethylene film, a nylon film, a polyvinyl chloride film and the like and it is preferable to be used after being treated with portioning treatment such as silicone treatment or Teflon treatment.

As the cover member 8 for protection of the conductive layer 9, usable are those capable of forming heat seal with the insulating layer resin and easy to be peeled and the foregoing films are layered in a plurality of the layers and coated with a sealing material suitable to the insulating layer resin in the sealing face to be used. The seal material is not particularly restricted if it is used for therapeutic care and usable are mainly ethylene-vinyl acetate copolymer, polyethylene, polypropylene, polyester and the like which may be used solely or as a mixture and based on necessity the following may be added further; styrene type polymer such as poly-$\alpha$-methylstyrene and polyvinyltoluene, terpene polymer such as $\alpha$-pinene polymer, resin blended with rosin or an inorganic filler such as talc. The portioning of the cover member 8 of the apparatus of invention is preferably the interface portioning between the insulating layer and the cover member. If polyester type resin is used for the insulating layer, it is preferable to select a seal material based on polyester resin. It is also preferable to set the 180 degree-portioning strength between 100 g to 1.500 g per 15 mm.

Incidentally, only water may be introduced to the conductive layer 9 of the iontophoresis device of the invention or depending on the cases, water may contain at least one of an ion exchange polymer, a foamed material, soft porous material such as sponge, and water-absorptive polymer. Further, in order to increase the conductivity, water may also contain an electrolytic substance such as sodium chloride, sodium carbonate, sodium citrate and a pH buffering agent.

As practical examples of the conductive layer 9 to be used for the invention, generally, pours membranes and foamed bodies such as a non-woven fabric, paper, gauze, defatted cotton, polyethylene or polypropylene having continuous foams, vinyl acetate, polyolefin foam, polyamide foam, polyurethane and the like; natural polysaccharides such as karaya gum, tragacanth gum, xanthane gum, starch, gum arabic, echo gum, locust bean gum, zelan gum, guar gum, carrageenan and the like; aqueous or water-soluble cellulose derivatives such as gelatin, pectin, agar, sodium alginate, polyvinyl alcohol and its partially saponified products, polyvinyl formal, polyvinyl ethyl ether and its copolymers, polyvinylpyrrolidone and its copolymers, polyacrylic acid sodium, sodium carboxymethyl cellulose, methyl cellulose, hydroxyethyl cellulose, hydroxy cellulose, hydroxypropyl methyl cellulose, hydroxypropyl cellulose, cellulose acetate phthalate and the like; and copolymers such as polycaboxyvinyl polymer, polyacrylamide and polyacrylamide derivatives, casein, albumin, chitin, chitosan, polyacrylic acid, polyacrylic acid sodium, polyhaemas, polyhaema derivatives, methoxyethylene-maleic anhydride copolymer, N-vinyl- acetamide, N-vinylacetamide copolymer with acrylic acid and/or acrylate, and their cross-linked products; water soluble polymer plasticized with ethylene glycol, glycerin and the like based on the necessity and their hydrogel, may be preferably used. Usable for the invention is not necessarily restricted to those. Further, the foregoing materials may be used in combination of two or more of them. Further, based on the necessity, they may be mixed with benzalconium chloride, bovine serum albumin (BSA), an anti-adsorption agent of polysorbet 80, and ion exchangeable polymer for the purpose of removing ion competing with the drugs.

Next, the adhesive sheet 10 in an iontophoresis device of the invention is a well-known plastic film for therapeutic care coated with an adhesive material and as the adhesive material, preferable to be used is a pressure-sensitive adhesive. As the pressure-sensitive adhesive, any pressure-sensitive adhesive may be used if an iontophoresis device of the invention can be held on the skin or the mucosa of a patient in contacting state and it is physiologically allowed to be used for the skin. Usable are, for example, an acrylic type adhesive such as poly-2-ethylhexyl acrylate, methacryl adhesive such as pulybutyle methacrylate, a silicone type adhesive such as polydimethylsiloxane, and a rubber type adhesive such as polyisobutyrene rubber, polybutadiene rubber, natural rubber, and the like. Also it is possible to add an tackifier and a softening agent based on necessity.

Figure 11:
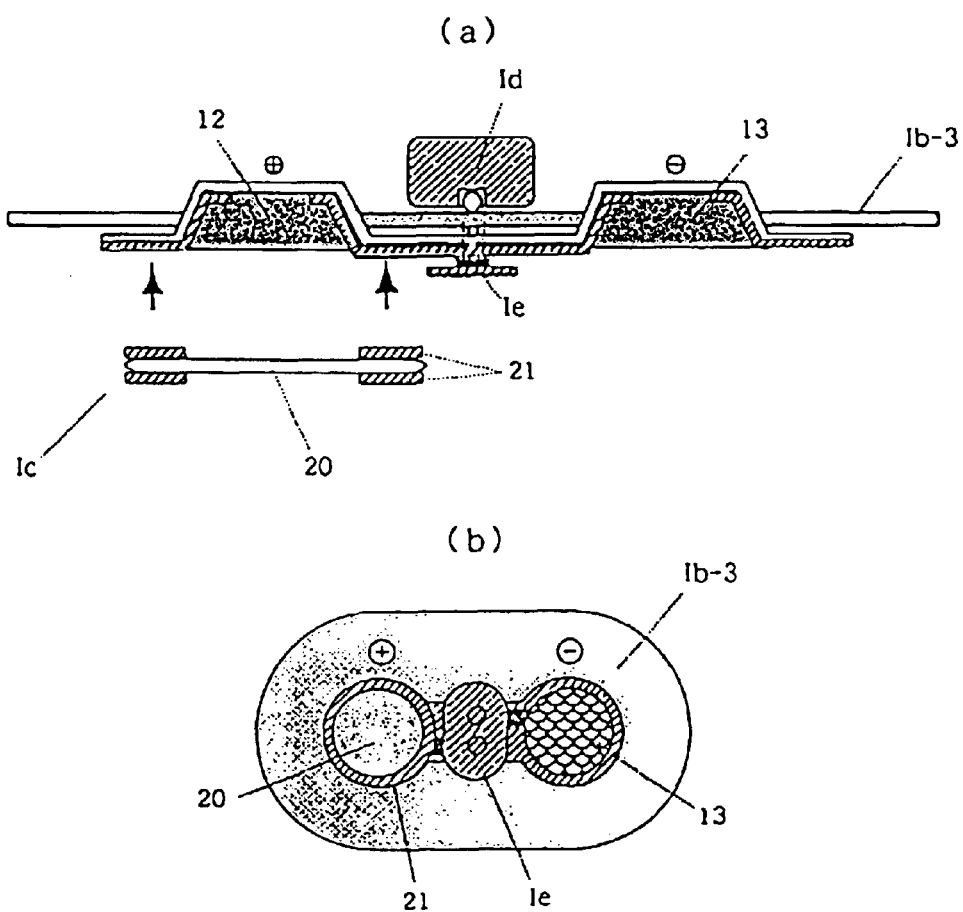
FIG. 11 is an illustration showing the use form of the integrated type electrode structure (Ib-3) according to the invention, (a) shows the cross-sectional view and (b) shows the rear side view.

The existence state of a drug in a device which is to be used in an iontophoresis device of the invention may be that the drug is contained while being dispersed or dissolved in the conductive layer 9 as shown in FIG. 3 or being contained in a drug storage portion 20 in dry sate and kept separately from the conductive layer as shown in the pharmaceutical portion (Ic) of FIG. 11 of a dissolution-at-use type apparatus and depending on the properties of the drugs and the functions of the apparatus, the existence state can be changed optionally. The drugs to be used for the invention will be listed up as follows.

Pharmaceutical agents to be used in the invention, any pharmaceutical agent in every curing field can be used if it is dissolved and dispersed in water and especially physiologically active substances with molecular weight of $1 \times 10^2$ to $1 \times 10^6$. For example, an anesthetic, an analgesic, an antianorexic, an anthelmintic, an antiasthmatic, an anticonvulsant, an antidiarrhoeica, an antimeoplastic agent, an antiparkinson drug, an antipruritic, a sympathomimetic agent, a xanthine derivative, an angiocardiac, e.g. a calcium channel blocker, an antipyretica, a β-bblocker, an antiarrhythmic, an antihypertensive drug, an antidiuretic, a vasodilator for the total body, coronary, peripheral and cerebrovascular systems, an anti-migraine drug, a motion sickness relief, an antiemetic, a central nervoussystem stimulant, an antitussive, a decogestant, a diagnostic drug, a hormone drug, a parasympatholytic agent, a parasympathomimetic agent, a psychostimulant, a sedative, a tranquilizer, an antiinflammatory agent, an antiarthritic, an antispasmodic, an antidepressant, an antipsychotic, an antidinic, an anxiolytic, an anesthetic antagonists, an antitumorigenic, a hypnotic, an immunosuppressor, a myasthenic, an antiviral drug, an antibiotic, an appetite suppressant, an antiemetic, an anticholilytic drug, an antihistamine, an anticonceptive, an antithrombotic drug, a bone absorption suppressant, and a bone formation accelerator, and the like may be exemplified, however they are not restricted to these examples. They may be used solely or in combinations based on necessity.

As examples of the respective drugs, steroids, for example, estradiol, progesterone, norgestrel, levonorgestrel, norethindrone, medroxyprogesterone acetate, testosterone and their derivatives such as esters and nitro compounds, for example, nitroglycerin, nitric isosorbites, nicotine, chlorophenylamine, terfenadine, triprolidine, and hydrocortizone; oxycam derivatives such as piroxicam; acetic acid and propione derivatives such as indomethacin, flurbiprofen, felbinac, diclofenac, ketoprofen, mucopolysaccharidase, e.g., thiomucase, buprenorphine, fentanyl, naloxone, codeine, lidocaine, dihydroergotamine, pizotyline, salbutamol, terbutaline, prostaglandins, e.g. mizoprostol, enprostil, omeprazole, imipramine, benzamides, e.g. metocloplasmin, scopolamine, clonidine, dihydropyridines, e.g. nifedipine, verapamil, ephedrine, pindolol, metoprolol, spironolactone, nicardipine hydrochloride, calcitriol, thiazides, e.g. hydrochlorothiazides, flunarizine, sydononimines, e.g. molsidomine, sulfuric polysaccharides e.g. heparin fraction, protein and peptides, e.g. insulin and its homologen, calcitonin and its homologen, e.g. elcatonin, protamine, glucagon, globulins, angiotensin I, angiotensin II, angiotensin III, represin, vasopressin, somatostatin and its homologen, growth hormone and oxytocin, and their salts of acids or bases pharmaceutically allowable these compounds based on necessity. Preferable are an anesthetic, hormons, protein, an analgesic, or other low molecular weight cations and more preferable ones are peptides, or polypeptides, e.g. insulin, calcitonin, gene peptides relevant to the calcitonin, vasopressin, desmopressin, protirelin (TRH), adrenocorticotropic hormone (ACTH), luteinizing hormone releasing hormone (LH-RH), growth hormone releasing hormone (GRH), nerve growth factor (NGF) and other releasing factors, angiotensin, parathyroid hormone (PTH), luteinizing hormone (LH), prolactin, serum gonadotropin, pituitary hormone (e.g. HGH, HMG, HCG), growth hormone, somatomedin, glucagon, oxytocin, gastrin, secretin, endorphin, enkephalin, endothelin, cholecystokinin, neurotensin, interferon, interleukin, transferrin, erythropoietin, superoxide dismutase (SOD), filgrastim (G-CSF), vasoactive intestinal polypeptide (VIP), muramyldipeptide, corticotropin, urogastrone, atrial natriuretic peptide hormone (h-ANP) and the like may be exemplified, however they are not restricted to these examples.

In the invention, the foregoing drugs and their salts may be contained solely or a plurality of these substances.

Figure 8:
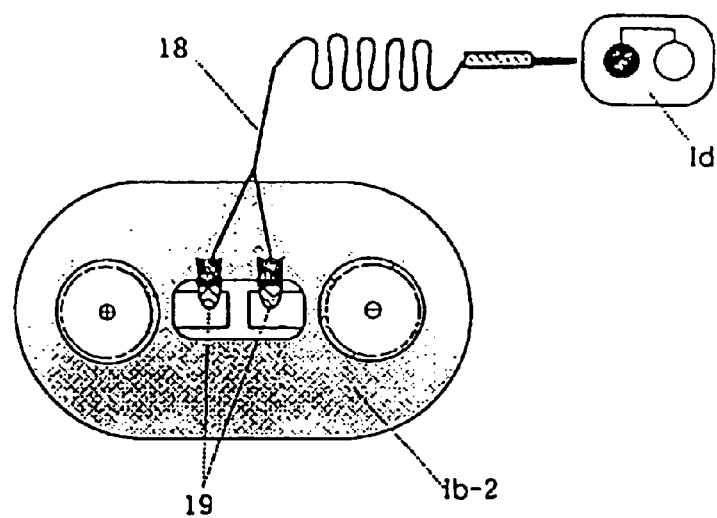
FIG. 8 is a figure showing the connection form between the integrated type electrode structure (lb-2) and an electric current output portion according to the invention.
Figure 9:
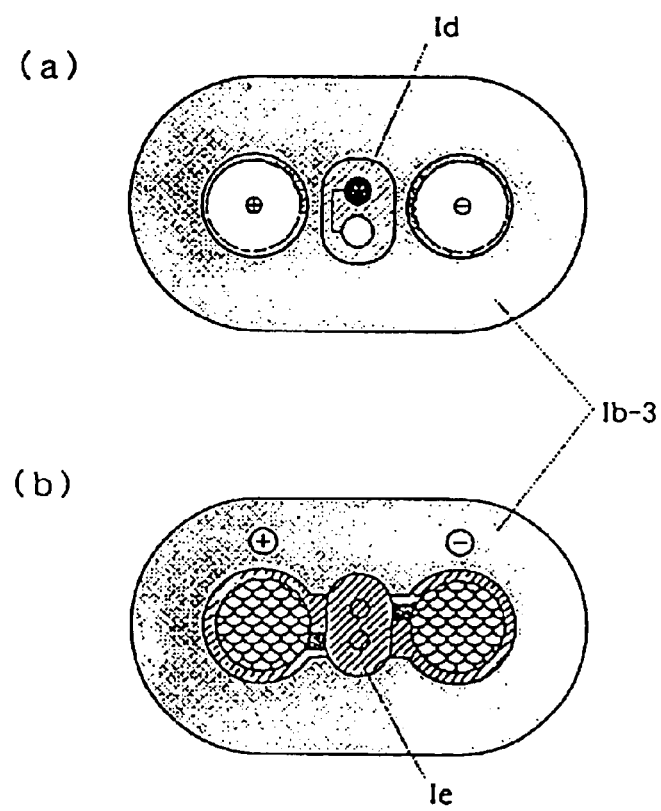
FIG. 9 is a figure showing the connection form between the integrated type electrode structure (lb-3) and an electric current output portion according to the invention, (a) shows the front view and (b) shows the back side view.

Further, regarding an electric current output portion (Id), an electric current control operation portion may be installed separately from an application portion as shown in FIG. 8 and may control the operation of the electrode portions through proper connection cord 18. Further a self-oscillation circuit in which a small battery is incorporated and a proper high voltage oscillation circuit connected with the oscillation circuit may be employed together and a small output portion (Id) in which both of such circuits are operated by control of a micro computer may be installed adjacently to the electrode portion as shown in FIG. 9 with a conductive snap connector (Ie) without using a connection cord.

Figure 7:
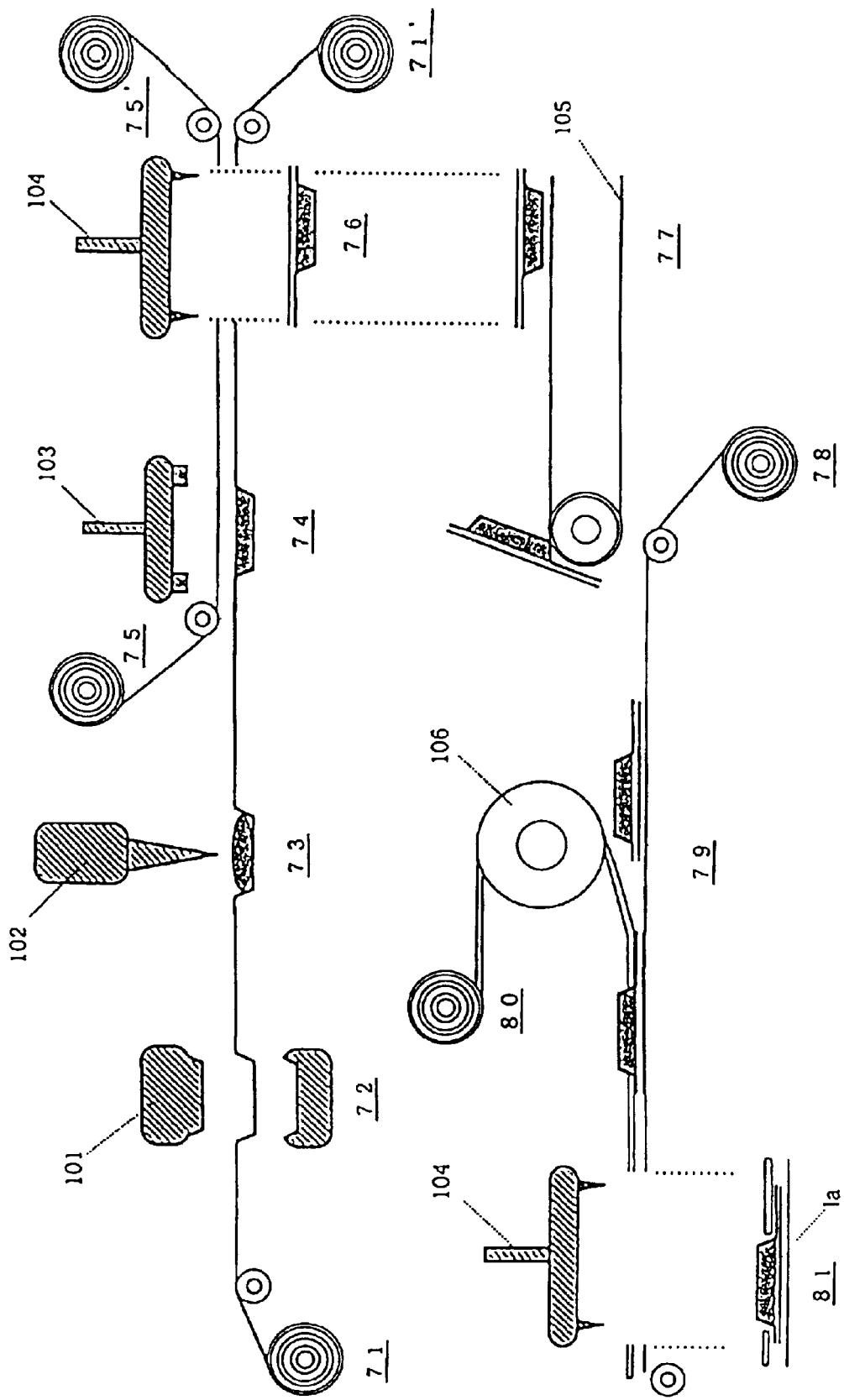
FIG. 7 shows a process flowchart for producing an electrode structure of an iontophoresis device according to the invention.

The electrode structure of a mass production type iontophoresis device constituted as described above according to the invention can be manufactured by combining innovative techniques and known techniques employed in pharmaceutical products and food, as shown, for example, in the manufacturing process flowchart of FIG. 7. The following is description of main steps.

1) A Step of Printing on the Substrate Film 1 for the Backing

The method for printing the electrode layer 2 and the insulating layer 3 on the substrate film 1 is carried out by employing a conventional printing technique such as screen printing, gravure printing and the like. Incidentally, regarding the electrode layer 2, also applicable are methods to produce the electrode layer 2, such as a method for spreading the an electrode material and fixing it, a method for evaporating the foregoing electrode material, and a method for photo-etching the foregoing electrode material.

2) A Step of Sheet Molding the Substrate Film for the Backing

The substrate film supplied from the rolling state is transported to a molding processing apparatus while the printing face being kept upside. In the molding processing apparatus, the processing position is controlled by a positioning sensor and when the electrode layer reaches a molding die, the transportation is stopped and the molding process is performed and then the substrate film is transported to the next step.

Incidentally, regarding the molding method, conventional techniques almost all involve steps of applying air pressure to a sheet softened by heating to the temperature at the glass transition point or higher and then fixing the shape by cooling after the deformation. In the manufacture method according to the invention, the characteristic point is that the sheet molding is carried out by cold processing at a temperature not higher than the thermal deformation temperature. Owing to that the cold processing is possible, the printing portions of the electrode layer 2 and the insulating layer 3 are scarcely affected and no problem such as substrate shrinkage at the time of molding takes place. Consequently, a mold portion can be formed at a high precision so as to form the molding form with the depth of 0.5 mm to 7.5 mm and the molding angle of 5 degree to 70 degree.

3) A Step of Filling the Conductive Layer

Although the conductive layer 9 differs depending on the embodiments, in this embodiment, description will be given of the case of filling a hydro-gel containing an electrolytic substance and a drug. The gel-filling is carried out by inserting a filling nozzle into a molding portion 31, which is a dent portion of the backing (Ia) and if the filling surface area is widened owing to use of a gel with gelling temperature is high or a gel with a high viscosity, the nozzle may be moved in XYZ axes to carry out pattern-filling. Further, after the filling, a step may be added to promote the gelling by physical cross-linking by cooling or by chemical cross-linking by light or heat.

4) A Step of Sealing the Cover Member

The cover member 8 is put on the conductive layer 9 to be sealed in the backing. The sealing method is preferable to be carried out using a heat seal and also an ultrasonic seal may be used in order to avoid deterioration of the gel components by sealing heat.

5) A Step of Cutting

The product obtained through the above described steps is independently cut by a cutter formed in an optional shape. Incidentally, this step may be carried out simultaneously in the sealing step of the seal material.

6) A Step of Installing the Adhesive Sheet and Cutting the Sheet

The independently cut electrode structure is transported on a film for liner treated with silicon and using a rotary type laminating apparatus, an adhesive sheet 10 is put on the electrode structure from the upper side and finally cut in a predetermined shape. Incidentally, the adhesive sheet 10 may previously be cut at a predetermined position for the purpose to avoid the backing lead portion from being covered with the adhesive sheet.

This manufacture method will be described in more detail in following examples.

Examples

Hereinafter, the electrode structure for the iontophoresis device of the invention and the method of producing the same will be described more particularly with reference to figures. At first, an example of the backing (Ia) of the electrode structure will be described below. (Examples 1 to 11 and comparative examples 1 to 4)

FIG. 1 shows an outlined figure of the backing (Ia) of the iontophoresis device according to the invention, (a) shows the front view, (b) shows the back side view, and (c) shows a cross-sectional view. FIG. 2 shows the substrate layer structure of the backing (Ia) of the iontophoresis device according to the invention, (a) shows section ① of FIG. 1 (c), (b) shows section ②, and (c) shows section ③. Further, FIG. 3 shows a schematic figure showing the basic embodiment of the electrode structure (Ib).

Regarding the manufacture of the backing (Ia) of the iontophoresis device of the invention, at first a plastic film 7 was dry-laminated on one face of a metal foil 6 using an isocyanate-cross-linked polyurethane adhesive and further the plastic film 7 was laminated on the other face in the same manner to manufacture a substrate film 1 for the backing. Next, a conductive silver paste ink (ED6036 manufactured by Acheson Japan Ltd.) was printed on one face of the plastic film 7 by screen printing and dried at 130° C for 5 minutes to form an electrode layer 2 with the thickness of 13 $\mu$m. Further an ink containing polyester resin 30 parts by weight, silica 3 parts by weight, and a thinner 100 parts by weight was screen-printed and dried at 130° C for 1 minutes to form an insulating layer 3 with the thickness of 10 $\mu$m. Incidentally, as shown in FIG. 1(c), the insulating layer 3 was so formed as not to cover the inner bottom of the molding portion 31 of the electrode layer 2 and some portion of the lead portion 11 to keep the effective diameter of the electrode layer in the bottom portion of the molding portion $\phi$ 18 mm. The molding portion 31 was inclined as to have the molding angle 4 and the sinking depth 5, the distance between the bottom portion of the molding portion 31 and the lead portion 11.

Next, sheet molding was carried out by a press from the electrode layer-printed face side in a manner that the electrode layer 2 (in the portion not covered with the insulator) was to be positioned in the bottom portion after molding and the shape of the molding portion 31 was adjusted to be $\phi$ 23 mm of the opening portion, $\phi$ 20.5 mm of the bottom portion, 1.8 mm of the sinking depth, and 50 degree of the molding angle. Also, in the following examples, as shown in FIG. 1, cutting was so carried out as to form one turn of an outward flange 32 in the circumference in the side where the electrode layer 2 was formed and as to install a backing lead portion 11 extended from a portion of the outward flange 32 outward in the radius direction.

Employing the above described manufacture method in common, backings of examples and comparative examples were manufactured as described in Table 1. In the following tables and descriptions, PET denotes a polyethylene terephthalate film, PVC denotes a poly(vinyl chloride) film, PP denotes a polypropylene film, and Al denotes an aluminum foil, respectively.

TABLE 1

| Example | A: plastic film (electrode-printed face) | B: metal foil | C: plastic film (backing outside) | Constitution ratio (A + C)/B | Substrate thickness | Processing temperature |
|---|---|---|---|---|---|---|
| Example 1 | PET (100 μm) | Al (15 μm) | PET (10 μm) | 7.33 | 125 μm | 180° C. |
| Example 2 | PET (100 μm) | Al (15 μm) | — | 6.67 | 115 μm | 180° C. |
| Example 3 | PET (100 μm) | Al (50 μm) | PET (100 μm) | 4.00 | 250 μm | 180° C. |
| Example 4 | PET (75 μm) | Al (50 μm) | PET (75 μm) | 3.00 | 200 μm | Room temperature |
| Example 5 | PET (100 μm) | Al (80 μm) | PET (100 μm) | 2.50 | 280 μm | 180° C. |
| Example 6 | PET (50 μm) | Al (50 μm) | PET (75 μm) | 2.50 | 175 μm | Room temperature |
| Example 7 | PET (75 μm) | Al (50 μm) | PET (50 μm) | 2.50 | 175 μm | Room temperature |
| Example 8 | PET (50 μm) | Al (50 μm) | PET (50 μm) | 2.00 | 150 μm | Room temperature |
| Example 9 | PET (38 μm) | Al (50 μm) | PET (38 μm) | 1.52 | 126 μm | Room temperature |
| Example 10 | PET (25 μm) | Al (50 μm) | PET (25 μm) | 1.00 | 100 μm | Room temperature |
| Example 11 | PET (25 μm) | Al (80 μm) | PET (25 μm) | 0.625 | 130 μm | Room temperature |
| Comparative example 1 | PET (100 μm) | — | — | — | 100 μm | 180° C. |
| Comparative example 2 | PET (200 μm) | — | — | — | 200 μm | 180° C. |
| Comparative example 3 | PVC (200 μm) | — | — | — | 200 μm | 180° C. |
| Comparative example 4 | PP (100 μm) | — | — | — | 200 μm | 120° C. |

Examples 12 to 19 and Comparative Example 5

The manufacture method for the following examples was approximately the same as the above described examples 1 to 11 and sheet molding was carried out in no-heating conditions from the electrode printed face side in a manner that the electrode layer 2 (the insulating layer was not formed yet) printed on the substrate film 1 for the backing was positioned in the bottom portion after molding and cutting was carried out to form the shape as shown in FIG. 1. Incidentally, in these examples, the constitution of the substrate film 1 for the backing was made common as same as that of the example 9, that is, PET (38 μm)/Al (50 μm)/PET (38 μm) and the molding portions of the respective examples were formed as to be φ23 mm of the opening portion, φ 20.5 mm of the bottom portion, and 1.0 to 2.4 mm of the sinking depth as shown in Table 2. Incidentally, the molding angle 4 was actually measured. Further, in the comparative example 5, PET (200 μm) was formed to be 1.2 mm of the sinking depth and 35 degree of the molding angle by heat-molding (preheating at 90° C. and molding at 180° C.).

TABLE 2

| Example | Substrate film | Sinking depth | Molding angle | Molding temperature |
|---|---|---|---|---|
| Example 12 | PET (38 μm)/Al (50 μm)/PET (38 μm) | 1.0 mm | 38.7 degree | Room temperature |
| Example 13 | Id. | 1.2 mm | 43.8 degree | Id. |
| Example 14 | Id. | 1.4 mm | 48.2 degree | Id. |
| Example 15 | Id. | 1.6 mm | 52.0 degree | Id. |
| Example 16 | Id. | 1.8 mm | 55.2 degree | Id. |
| Example 17 | Id. | 2.0 mm | 60.1 degree | Id. |
| Example 18 | Id. | 2.2 mm | 65.6 degree | Id. |
| Example 19 | Id. | 2.4 mm | 68.5 degree | Id. |
| Comparative example 5 | PET (200 μm) | 1.2 mm | 35.0 degree | 180° C. |

(Experiment 1)

Regarding the backing of the examples 1 to 11 and the comparative examples 1 to 4, the uniformity of the processed products, the flexibility of the backings to the skin, and the strength of the molding portions were sensuously evaluated. Incidentally the judgment standards are as follows.

Further if the processing temperature was high, since the effect was caused on the printed portions such as electrode layers, the total evaluation of the substrate films for the backings was performed while taking the processing temperature into consideration. The evaluation results are shown in Table 3.

<Uniformity of the processed products>

Having high uniformity: ⊚, having not so high uniformity but no practical problem for use: ○, having deformation in some portion and problematic for use: Δ, considerably shrunk and deformed and difficult to be used: ×.

<Flexibility of the processed products>

No hardness and no unpleasant feeling: ⊚, slightly hard feeling but no unpleasant feeling: ○, hard feeling and unpleasant feeling: Δ, hard and no flexibility and impossible to be attached to the skin: ×.

<Strength of the processed products>

No deformation even with intense impact: ⊚, slightly deformed with strong impact but sufficient to protect the conductive layer: ○, weak strength insufficient to protect the conductive layer: Δ, deformed even with weak impact impossible to protect the conductive layer: ×.

<Synthetic judgment>

Good physical properties: ⊚, slightly problematic but usable physical properties: ○, hard to be said to have good physical properties and limited for use: Δ, impossible to be used: ×.

TABLE 3

| Example | Processing temperature | Uniformity of processed product | Softness of processed product | Strength of processed product | Synthetic judgment |
|---|---|---|---|---|---|
| Example 1 | 180° C. | ○ | Δ | Δ | Δ |
| Example 2 | 180° C. | ○ | ○ | × | Δ |
| Example 3 | 180° C. | ○ | Δ | ○ | Δ |
| Example 4 | Room temperature | ○ | ○ | ○ | ○ |

TABLE 3-continued

| Example | Processing temperature | Uniformity of processed product | Softness of processed product | Strength of processed product | Synthetic judgment |
|---|---|---|---|---|---|
| Example 5 | 180° C. | ○ | Δ | ○ | x |
| Example 6 | Room temperature | ○ | ○ | ○ | ◎ |
| Example 7 | Room temperature | ○ | ○ | ○ | ◎ |
| Example 8 | Room temperature | ◎ | ◎ | ○ | ◎ |
| Example 9 | Room temperature | ◎ | ◎ | ○ | ◎ |
| Example 10 | Room temperature | Δ | ◎ | Δ | Δ |
| Example 11 | Room temperature | x | ◎ | x | x |
| Comparative example 1 | 180° C. | ◎ | ○ | Δ | Δ |
| Comparative example 2 | 180° C. | ◎ | ○ | ○ | Δ |
| Comparative example 3 | 180° C. | ◎ | Δ | ○ | Δ |
| Comparative example 4 | 120° C. | x | ◎ | x | x |

(Remark)
Examples 1 to 3, 5 and comparative examples 1 to 4: molding at a room temperature could not be carried out and processing was carried out by heat-molding.

As the evaluation results, in the examples 1 to 3 and the comparative examples 1 to 4 in which the constitution ratio of the plastic film to the metal foil was 4.00 or higher, heating at 120° C. or higher was required for the molding regardless of the thickness of the substrate. On the other hand, in the examples 4 to 7 in which the constitution ratio was 2.50 to 3.00, molding without heating was possible if the thickness of the substrate was 200 μm or thinner.

The uniformity of the processed product was good in the case of examples in which the constitution ratio of polyethylene terephthalate hard to be thermally decomposed was high, whereas significant deformation was observed in the processed products of the example 11 and the comparative example 4 in which polyethylene or polypropylene was layered. The flexibility was excellent in the examples 8 to 11 in which the constitution ratio of the plastic film to the metal foil was 2.00 or lower and the thickness of the substrate was 150 μm or thinner. Although the strength of the molding portion differed depending on the constitution of the substrate, it was found that the thickness of the substrate was required to be at least 125 μm or thicker in order to protect the conductive layer.

Consequently based on the results, it could be concluded that all of the factors were approximately satisfactory in the case of the substrate constitutions of the examples 6 to 9.

(Experiment 2)

Regarding the backings of the examples 3, 7, 8, 9, 11 and the comparative examples 2, 4, the impedance of each electrode layer 2 was measured to investigate the probability of damages and electric insulation of the electrode layer depending on the processing temperature at the time of the molding process. The evaluation results are shown in Table 4. Further, the same measurement was carried out for the backing of the examples 12 to 19 and the comparative example 5 to investigate the probability of damages and electric insulation of the electrode layer depending on the molding angle 4. The evaluation results are shown in Table 5.

Figure 10:
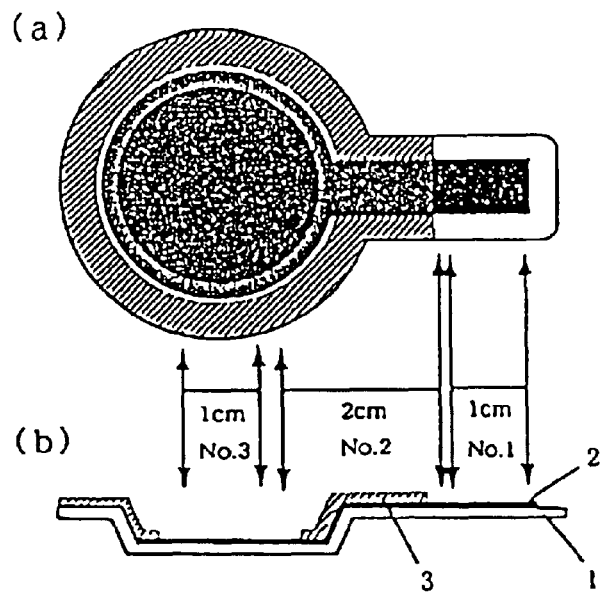
FIG. 10 is an illustration showing the impedance measuring points (a) and (b) in a backing.

The impedance measurement of the examples was carried out at the points of No. 1 to No. 3 shown in the (a) rear side figure and the (b) cross-sectional figure in the backing shown in FIG. 10, using LCZ meter (manufactured by N. F. Circuit Design Block Co.). The point No. 1 was a part of a lead portion where the electrode layer 2 was exposed and had 1 cm width; the point No. 2 was a part from the lead portion to the molding portion sandwiching the insulating layer 3 and had 2 cm width; and the point No. 3 was a part in the bottom portion of the molding portion where the electrode layer 2 was exposed and had 1 cm width. The measurement conditions were controlled as follows.

<LCZ meter measurement conditions>Display A: |Z|, speed: slow, test lead: 2326 A, frequency: 1 kHz, circuit: SER, level: 1 V, time (measurement duration): 3 min.

TABLE 4

| Example | Processing temperature | Molding angle | Impedance (unit: mΩ) | | |
|---|---|---|---|---|---|
| | | | No. 1 | No. 2 | No. 3 |
| Example 3 | 180° C. | 50 degree | 149.4 ± 22.6 | 407.5 ± 650.1 (Ω) | 53.2 ± 65.1 (Ω) |
| Example 7 | Room temperature | 50 degree | 107.9 ± 21.9 | 454.8 ± 32.9 | 399.9 ± 58.5 |
| Example 8 | Room temperature | 50 degree | 98.2 ± 10.5 | 481.3 ± 114.0 | 312.1 ± 14.6 |
| Example 9 | Room temperature | 50 degree | 84.6 ± 9.9 | 356.1 ± 42.1 | 192.1 ± 13.6 |
| Example 11 | Room temperature | 50 degree | 125.6 ± 4.0 | 271.2 ± 15.9 | 143.7 ± 5.2 |
| Comparative example 2 | 180° C. | 50 degree | 108.0 ± 6.3 | 5.7 ± 1.8 (MΩ) | 281.6 ± 203.5 (Ω) |
| Comparative example 4 | 120° C. | 50 degree | 102.3 ± 2.9 | 14.6 ± 4.5 (MΩ) | 1032.6 ± 65.1 (Ω) |

According to the results shown in Table 4, in any example or comparative example, impedance was found increasing in the boundary (No. 2) between the molding portion and the non-molding portion, and the bottom portion (No. 3) of the molding portion as compared with the non-molding portion (No. 1). That was supposed to be attributed to deterioration of the electrode layer by heating at the time of sheet molding and occurrence of cracking in the surface of the electrode layer owing to the film expansion. However, as shown in the case of backings of the examples 7. 8, 9, 11 which were possible to be molded at a room temperature, the impedance increase was within mΩ level. On the other hand, in the case of the 15 comparative examples 2, 4 where heat-molding at 180° C. was required, the increase was MΩ level to make it clear that the electrode layer was almost in disconnected state. According to the results, it was found that the damage of the electrode layer by the molding process could be prevented and the substrate constitution could sufficiently stand the manufacture process in mass production if the substrate had the substrate constitution of the invention possible to be molded at a room temperature.

TABLE 5

| Example | Sinking depth | Molding angle | Impedance (unit: mΩ) | | |
|---|---|---|---|---|---|
| | | | No. 1 | No. 2 | No. 3 |
| Example 12 | 1.0 mm | 38.7 degree | 86.5 ± 2.2 | 208.4 ± 7.9 | 91.1 ± 7.6 |
| Example 13 | 1.2 mm | 43.8 degree | 88.5 ± 3.9 | 226.1 ± 7.6 | 108.7 ± 10.8 |
| Example 14 | 1.4 mm | 48.2 degree | 86.2 ± 4.7 | 250.7 ± 14.6 | 124.0 ± 11.4 |

TABLE 5-continued

| Example | Sinking depth | Molding angle | Impedance (unit: mΩ) | | |
|---|---|---|---|---|---|
| | | | No. 1 | No. 2 | No. 3 |
| Example 15 | 1.6 mm | 52.0 degree | 85.9 ± 3.8 | 317.6 ± 8.4 | 174.5 ± 3.0 |
| Example 16 | 1.8 mm | 55.2 degree | 83.0 ± 0.6 | 367.1 ± 29.3 | 215.3 ± 20.0 |
| Example 17 | 2.0 mm | 60.1 degree | 89.2 ± 2.4 | 700.6 ± 34.8 | 495.9 ± 12.1 |
| Example 18 | 2.2 mm | 65.6 degree | 88.2 ± 1.0 | 1058.7 ± 26.0 | 779.9 ± 5.2 |
| Example 19 | 2.4 mm | 68.5 degree | 88.8 ± 2.5 | 1564.2 ± 42.0 | 1152.3 ± 34.1 |
| Comparative example 5 | 1.2 mm | 35.0 degree | 84.5 ± 2.9 | 3.44 ± 1.3 (MΩ) | 332.6 ± 35.1 (Ω) |

According to the results shown in Table 5, it was confirmed that the impedance increase was within in mΩ level even if the molding angle 4 was around 70 degree (example 19) in the case of the substrate film 1 for the backing of the invention. On the other hand, in the case of PET in the comparative example 5, increase was observed in MΩ level at the time when the molding angle reached 35 degree. Like this, it was made possible to carry out sheet-molding at a high angle while the effect on the electrode layer being suppressed to the minimum level in the case of the substrate film 1 for the backing of the invention.

Further, taking the flexibility to the skin, it is preferable to keep the molding angle 4 be 70 degree or lower, the molding possibility of the substrate film 1 of the backing of the invention can be judged to be sufficient.

Example 20

According to the manufacture process shown in the FIG. 7, FIG. 4 and FIG. 5 show the examples of the separation type electrode structure of which an anode and a cathode were independently produced in an iontophoresis device of the invention. As shown in the figures, an adhesive sheet 10 was formed in the front face of the substrate film 1. Further, an anode side conductive layer 12 was formed in the molding portion in the anode side and a cathode side conductive layer 13 was formed in the molding portion in the cathode side, respectively. An anode side electrode layer 14 and a cathode side electrode layer 15 were respectively led to lead portions 11 from inner bottom portions of respective molding portions and insulating layers 3 were formed in the outer circumferential portions of the respective molding portions. Cover members 8 were so disposed as to carrying out sealing between the insulating layers 3 and themselves. Liners 16 for adhesive sheets were put thereon. In the electrode structure shown in FIG. 5, each cover member 8 was made to be a monolayer structure as to work as the cover member for the backing and the liner 16 of the adhesive sheet, however each cover member 8 and the liner 16 could be formed in a double layer structure as same in the case of the electrode structure shown in FIG. 4. Further, each clip portion 19 of each connection cord 18 to be connected to an electric current output portion (Id) was connected to each lead portion 11 as shown in FIG. 8. Hereinafter, the manufacture example will be described.

1) Production of the Substrate Film for the Backing

A polyethylene terephthalate (PET) of 38 μm thickness was dry-laminated on one face of an aluminum foil (Al) of 50 μm thickness using an isocyanate cross-linked polyurethane adhesive and a polyethylene terephthalate of 38 μm thickness was laminated on the other face in the same manner to produce the substrate film 1 in rolled state. Next, at the time of producing an anode, a silver paste ink (ED6036 manufactured by Acheson Japan Ltd.) and at the time of producing a cathode, a silver/silver chloride paste ink (ED6036 manufactured by Acheson Japan Ltd.) were respectively printed on one face of the polyester film by rotary screen printing and dried at 130° C. for 5 minutes to form electrode layers (14, 15) with the thickness of 13 μm. Further an ink containing polyester resin 30 parts by weight, silica 3 parts by weight, and a thinner 100 parts by weight was rotary screen-printed and dried at 130° C. for 1 minute to form an insulating layer 3 with the thickness of 10 μm. Incidentally, the printing pattern was same as shown in FIG. 1 and the obtained substrate film (in the rolled state) had the diameter of the electrode layers (the bottom parts of the molding portions) was φ 18 mm, 2) A Step of Molding the Sheet of the Substrate Film for the Backing The substrate film supplied from the rolled state in a backing substrate supply portion 71 as shown in FIG. 7 was transported to the inside of a molding processing apparatus 101 in a sheet processing section while the printing face being kept upside. While the processing position being controlled by a positioning sensor which was not illustrated, the sheet-molding was carried out in no-heating condition. The molding shape was adjusted to be φ 23 mm of the opening portion, φ 20.5 mm of the bottom portion, 1.8 mm of the sinking depth, and 50 degree of the molding angle.

3) Production of the Conductive Layer

Components disclosed in Table 6 were respectively produced for the conductive layers (12, 13) of the anode and the cathode. For the anode side conductive layer 12, components were prepared by dispersing and swelling agar and ion exchange resin at a room temperature for 1 hour by an agitating and homogenizing mixer and heating at 90° C for 1 hour and successively keeping the resulting mixture at 70° C. in a hopper of a filling apparatus 102 in a conductive layer filling portion 73. On the other hand, for the cathode side conductive layer 13, components were prepared by mixing polyvinyl alcohol, sodium chloride, and distilled water for injection and then thermally dissolving them at 120° C. for 15 minutes in an autoclave and successively keeping the resulting solution at a room temperature in a hopper of the filling apparatus 102.

TABLE 6

| Anode portion | | Cathode portion | |
|---|---|---|---|
| Components | Content (w/w %) | Components | Content (w/w %) |
| Agar | 1.0 | Polyvinyl alcohol | 12.0 |
| Ion exchange resin (cholestyramine) | 5.0 | Sodium chloride | 0.9 |
| Distilled water for injection | 94.0 | Distilled water for injection | 87.1 |
| Total | 100.0 | Total | 100.0 |

3) A Filling Step of the Conductive Layer, and a Sealing and Cutting Step of the Cover Member On completion of the sheet molding, 0.8 g of each conductive layer component was evenly packed in the molding portion of the substrate using the filling apparatus 102. Next, in a seal processed portion 74, an Al laminate cover member 8 coated with a PET-based sealant was supplied from a cover member supply portion 75, put on the conductive layer, and sealed on the backing in the conditions of 195° C. sealing temperature, 3.0 kgf/cm² sealing pressure, and 1.5 second sealing duration using a heat sealing apparatus 103. Further, after sealing, cutting was carried out in a punching process portion 76 using a cutting apparatus 104 to obtain an electrode structure with the shape as shown in FIG. 1. Incidentally, behind the punching process portion 76, a backing substrate discharging portion 71' and a cover member 75' were installed.

4) A Step of Installing the Adhesive Sheet

Each of the respectively cut electrode structure bodies was transported on a silicon-treated PET film of 75 μm thickness supplied from a line supply portion 78 using a transporting apparatus 105 of a processed product transporting portion 77 and further using a seat setting apparatus 106 in an adhesive sheet attachment portion 79, a therapeutic adhesive tape (Microfoam ™ (manufactured by 3M Co.)) supplied from the upper side from an adhesive sheet supply portion 80 was put thereon, and cutting was again carried out in a punching process portion 81 in the final step to obtain the electrode structure (Ib-1) shown in FIG. 4. In the case of the electrode structure (Ib-2) shown in FIG. 5, the anode and the cathode were simultaneously supplied and transported and the adhesive sheet 10 was put on.

Incidentally, the connection form with the electric current output portion (Id) of the invention was as shown in FIG. 8, and there was left portions where no adhesive sheet was installed so as to carry out connection after attachment to the skin and from that portion, clip portions 19 of connection cords 18 were thus enabled to be installed in the backing lead portions 11.

Example 21

According to the manufacture process shown in FIG. 7, FIG. 6 shows an example of the integrated type electrode structure of which an anode and a cathode were integrally produced in an iontophoresis device of the invention. As shown in the figure, an adhesive sheet 10 was formed in the front face of the substrate film 1. Further, an anode side conductive layer 12 was formed in the molding portion in the anode side and a cathode side conductive layer 13 was formed in the molding portion in the cathode side, respectively. An anode side electrode layer 14 and a cathode side electrode layer 15 were respectively led to lead portions from inner bottom portions of respective molding portions. Insulating layers 3 were formed respectively in the outer circumferential portions of the respective molding portions. Cover members 8 were so disposed as to carrying out sealing between the insulating layers 3 and themselves. Liners 16 for adhesive sheets were put thereon.

Insertion inlets 17 (one each in the anode side and the cathode side) for conductive snap connectors were formed in the lead portions and the cover members 8 of the respective electrode layers 14, 15 and as shown in FIG. 9 and FIG. 11, electricity was enabled to be communicated by sandwiching the electrode structure with the conductive snap connectors (Ie) and the electric current output portion (Id).

Hereinafter, the manufacture example will be described. The manufacture method of this example was almost the same as that of the example 20, however, being different from the example 20, the respective steps of printing, processing, and filling the conductive layers were carried out simultaneously for the anode and the cathode and as compared with those of the example 20, the electrode structure was manufactured in steps in about a half in the number of the entire steps. Incidentally, the forms of both electrodes were same and the molding shape was adjust to be φ 25 mm of the opening portion, φ 22 mm of the bottom portion, 1.8 mm of the sinking depth, and 50 degree of the molding angle, 1.8 g of the conductive layer-filling amount, and φ 21 mm of the electrode layer printing pattern of the bottom portion in the molding portion.

(Experiment 3)

In this example, the salmon calcitonin concentration in blood of rats was measured actually using the dissolving-at-use type agent by the apparatus of the example 21.

Incidentally, each of the pharmaceutical portions (Ic) was composed of the drug storage membrane 20 and the adhesive layer 21 in the periphery of the pharmaceutical portion as shown in FIG. 11(a), (b). The pharmaceutical portions (IC) were stuck to the electrode structure (Ib-3) so as to brought the drug storage membrane 20 into contact with the anode side conductive layer 12 at the using time. In this experiment, the drug storage membrane 20 (Biodyne +, produced by Ball Co.) of φ 28 mm in FIG. 11 was used for the experiment after being impregnated with salmon calcitonin 10 IU (2 μg) by dropwise titrating it to the membrane and drying the resulting membrane.

At the time of starting the experiment, as shown in FIG. 11, the drug storage membrane was attached to the anode of the apparatus of the example 21 and the drug storage membrane was hydrated and then the electrodes were attached to the shaved abdominal regions of SD male rats (7-week oil) under anesthesia and using the anode as a donor electrode and the cathode as a reference electrode, pulsed de-polarized electric communication (frequency: 30 kHz, on/off: 3/7, voltage: 10 V) was carried out for 45 minutes from the electric current output portion. Incidentally, the conductive snap connector (Ie) was used for the connection of the electrode structure (Ib-3) and the electric current output portion (Id).

The concentration of salmon calcitonin in serum was measured using a radioimmunoassay kit (peninsular salmon calcitonin measurement kit) by collecting blood from jugular veins time to time. The results are shown in FIG. 12.

Figure 12:
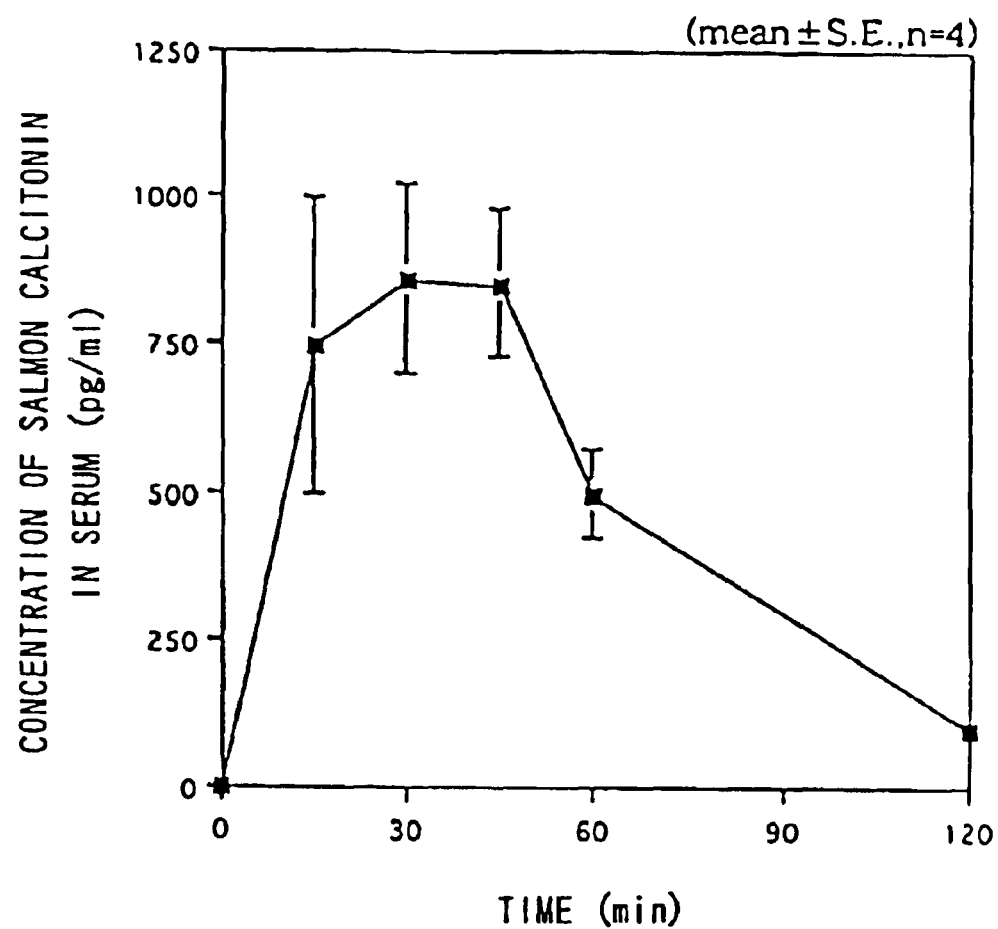
FIG. 12 is a graph showing the change of the concentration of salmon calcitonin in serum of a rat with the lapse of time.

According to the results shown in FIG. 12, the concentration of salmon calcitonin in serum was 849.6±124.5 pg/ml (the average value ± standard error) after 45 minutes and found gradually decreased after electric communication. According to the result, it was implied that the electrode structure of the invention sufficiently have the capability as an iontophoresis device.

(Experiment 4)

In this experiment, the peel strength of the cover member relative to the agent in the anode side of the apparatus of the example 20 was measured by carrying out 90 degree delamination of the cover member. Table 7 shows the detailed seal design and the measurement results. Next, using the same agent, the sensuous test was performed for the peeling tough and peeled state at the time of peeling the cover member. The results are shown in Table 8. In order to verify the sealing property, using the agent of this experiment was subjected to a water evaporation test. The water evaporation test was carried out by measuring the change of the water content in the agent kept at 60° C. and 40° C. with the lapse of time for the evaluation. The results are shown in Table 9.

TABLE 7

| Backing | PET 38 μm/Al 50 μm/PET 38 μm/Ag 13 μm/polyester resin 10 μm (seal face) |
|---|---|
| Cover member | PET 12 μm/Al 15 μm/PET 60 μm/PET type sealant 35 μm (seal face) |
| Seal type | circular (inner diameter 24 mm, outer diameter 32 mm, ring width 4 mm) |

TABLE 7-continued

| | |
|---|---|
| 90-degree peel strength (entire delamination) | 188.4 ± 62.8 g (3 point, mean ± S.D.) (Max.) 242.0 g. (Min.) 119.3 g |

(Remark)
Peel strength measurement apparatus: rheometer CR300 (produced by Sun Science Co.), peeling speed: 60 mm/min

TABLE 8

| Investigation item | Investigation result | |
|---|---|---|
| 1) Investigation performed for peel strength of the cover member (20 volunteers involved) | Persons who felt intensely strong | (0) |
| | Persons who felt slightly strong | (2) |
| | Persons who felt proper | (17) |
| | Persons who felt weak | (1) |
| | Persons who felt considerable weak | (0) |
| 2) Investigation performed for peeling mechanism of the cover member (20 volunteers involved) | Persons who confirmed interfacial separation | (20) |
| | Persons who confirmed interlayer separation | (0) |
| | Persons who confirmed coagulation separation | (0) |
| 3) Investigation performed for occurrence of damage in the electrode layer printed face after peeling the cover member (20 volunteers involved) | Damage occurring | (0) |
| | No damage occurring | (20) |

TABLE 9

| Standstill conditions | | Decrease ratio of water content (n = 3, mean ± S.D.) |
|---|---|---|
| 60° C., 75% R.H. | 2 weeks | −0.01 ± 0.02% |
| | 1 month | −0.06 ± 0.02% |
| 40° C., 75% R.H. | 1 month | 0.01 ± 0.04% |
| | 3 months | −0.01 ± 0.01% |
| | 6 months | −0.05 ± 0.03% |

The 90-degree peel strength of the cover member of the invention was about 200 g and the value was supported as a proper strength in the sensuous test. Further, since the peeling mechanism was interfacial separation, no damage was observed in the electrode layer printing face. Further, according to the results of the water evaporation test, the water evaporation prevention was confirmed to be almost 100% possible.

According to the above described results, the agent of the invention is excellent in operation property and capable of retain the contents in the conductive layer in stable state.

Industrial Applicability

Since an iontophoresis device of the invention has the above described technical constitutions, it can provide the following excellent effects.

Regarding a backing of the invention, pattern printing is possible for an electrode layer and an insulating layer and sheet molding is also possible in non-heating condition, so that electric current can be supplied to a conductive layer without requiring connection means such as electrode terminals or the like and that makes the iontophoresis device excellent in economical property and mass productivity. Further, owing to the installation of the insulating layer, the contact of the electrode layer with the skin can be prevented and also, the electrode layer is prevented from damages at the time of molding process of the backing.

Further, the insulating layer is provided with a function also as a seal material for sealing the cover member, long time storage of the content of the electrode layer is made possible. Further, since an easy peel method based on interfacial peeling is employed in order to prevent damages of the electrode layer at the time of peeling the cover member. the operability at the time of peeling the cover member is easy.

Further, since the substrate film for the backing has a substrate constitution with high bending property and also shape-retaining property for retaining the bent state, highly close adhesion can be achieved at the time of attachment to the skin. Based on the above described results, according to the invention, it is made possible to provide an electrode structure for an iontophoresis device and a method of producing the electrode structure, excellent in the economical property, operation property, stability, and safety.

What is claimed is:

1. An electrode structure for an iontophoresis device comprising:

a backing having a substrate film having a molding portion, an electrode layer formed passing the outer circumferential portion from the inner bottom of the molding portion, an insulating layer formed on at least the outer circumferential portion of the molding portion and also on the upper portion of the electrode layer, a conductive layer disposed in the molding portion, and a cover member made of water-impermeable material for covering the conductive layer and the insulating layer wherein the cover member seals the insulating layer formed on the outer circumferential portion of the molding portion in a separable manner, thereby allowing the conductive layer disposed in the molding portion to be kept in a sealed state.

2. The electrode structure for the iontophoresis device according to claim 1, wherein an adhesive sheet is installed in the rear face of the substrate film of the backing.

3. The electrode structure for the iontophoresis device according to claim 1, wherein the sinking depth in the molding portion of the substrate film is in a range of 0.5 mm to 7.5 mm.

4. The electrode structure for the iontophoresis device according to claim 1, wherein the molding angle in the molding portion of the substrate film is in a range of 5° to 70°.

5. The electrode structure for the iontophoresis device according to claim 1, wherein the separation mechanism between the insulating layer and the cover member is interfacial separation.

6. The electrode structure for the iontophoresis device according to claim 5, wherein the 180 degree-peel strength between the insulating layer and the cover member is in a range of 100 g to 1,500 g per 15 mm.

7. An electrode structure for an iontophoresis device comprising:

a backing having a substrate film provided with a molding portion having a dent, a flange portion formed in the outer circumferential portion of the molding portion, and a lead portion led out of the flange portion, an electrode layer formed from the inner bottom of the molding portion to the lead portion through the flange portion, and an insulating layer formed on at least the flange portion and also on the upper portion of the electrode layer;

a conductive layer disposed in the molding portion;

and a cover member made of water-impermeable material for sealing the insulating layer formed on the flange portion in a separable manner to allow the conductive layer disposed in the molding portion to be kept in a sealed state.

8. The electrode structure for the iontophoresis device according to claim 7, wherein the lead portion formed in the electrode layer is so composed as to be connected with the clip portion of a connection cord.

9. The electrode structure for the iontophoresis device according to claim 7, wherein the lead portion formed in the electrode layer has an insertion inlet for a connector.

10. A method of producing an electrode structure for an iontophoresis device comprising (a) a step of printing a conductive layer and an insulating layer on a substrate film, (b) a step of forming a molding portion in the substrate film in a manner that the insulating layer is positioned at least on an outer circumferential portion, (c) a step of disposing a conductive layer in the molding portion, (d) a step of supplying a cover member made of water-impermeable material to the substrate film and sealing between the insulating layer positioned in the outer circumferential portion and the cover member to allow the conductive layer disposed in the molding portion to be kept in a sealed state, and (e) a step of cutting the substrate film and the cover member in a predetermined shape.

11. The method of producing the electrode structure for the iontophoresis device according to claim 10, wherein at least the steps (b) to (e) are carried out in a continuous line.

12. The method of producing the electrode structure for the iontophoresis device according to claim 10, wherein the method further comprises a step of supplying an adhesive sheet to the rear face of the substrate film and cutting the sheet into a predetermined shape.

13. The method of producing the electrode structure for the iontophoresis device according to claim 10, wherein the step of forming the molding portion is carried out while a convexity portion of a press die being butted to at least the electrode layer on the substrate film.

14. The method of producing the electrode structure for the iontophoresis device according to claim 10, wherein the step of forming the molding portion in the substrate film is carried out by cold processing at a temperature lower than the thermal deformation.

15. The method of producing the electrode structure for the iontophoresis device according to claim 10, wherein the step of disposing the conductive layer to the molding portion includes a step of promoting gelling of conductive gel composing the conductive layer.

16. The method of producing the electrode structure for the iontophoresis device according to claim 15, wherein the step of promoting the gelling is to promote gelling by physical cross-linking by cooling or chemical cross-linking by light or heat.

* * * * *